United States Patent
Boday et al.

(10) Patent No.: US 9,245,202 B2
(45) Date of Patent: Jan. 26, 2016

(54) TAMPER DETECTION WITH MICROCASPULE RUPTURE

(71) Applicant: International Business Machines Corporation, Armonk, NY (US)

(72) Inventors: Dylan J. Boday, Tucson, AZ (US); Jason T. Wertz, Wappingers Falls, NY (US)

(73) Assignee: International Business Machines Corporation, Armonk, NY (US)

(*) Notice: Subject to any disclaimer, the term of this patent is extended or adjusted under 35 U.S.C. 154(b) by 109 days.

(21) Appl. No.: 13/911,430

(22) Filed: Jun. 6, 2013

(65) Prior Publication Data

US 2014/0363091 A1   Dec. 11, 2014

(51) Int. Cl.
G06K 9/68 (2006.01)
G06K 9/62 (2006.01)
G01N 21/64 (2006.01)

(52) U.S. Cl.
CPC .......... G06K 9/6202 (2013.01); G01N 21/6447 (2013.01); G01N 2021/6439 (2013.01); G06K 9/68 (2013.01)

(58) Field of Classification Search
USPC ............. 382/218; 235/454, 380, 381; 283/81, 283/82, 72, 94, 103; 713/170, 176, 179
See application file for complete search history.

(56) References Cited

U.S. PATENT DOCUMENTS

| | | | |
|---|---|---|---|
| 4,273,671 A * | 6/1981 | Allinikov | 252/301.19 |
| 5,325,721 A | 7/1994 | Pendergrass, Jr. | |
| 5,441,843 A * | 8/1995 | Hara | 430/138 |
| 5,827,531 A * | 10/1998 | Morrison et al. | 424/450 |
| 6,047,964 A | 4/2000 | Lawandy et al. | |
| 7,005,733 B2 | 2/2006 | Kommerling et al. | |
| 7,129,166 B2 | 10/2006 | Speakman | |
| 7,153,557 B2 | 12/2006 | Rancien | |
| 2002/0179718 A1 | 12/2002 | Murokh et al. | |
| 2004/0058381 A1* | 3/2004 | Roitman | 435/7.1 |
| 2004/0178734 A1* | 9/2004 | Nagasaki et al. | 313/634 |
| 2005/0084788 A1* | 4/2005 | Yau et al. | 430/138 |
| 2007/0012784 A1* | 1/2007 | Mercolino | 235/491 |
| 2007/0286644 A1* | 12/2007 | Takegawa | 399/159 |
| 2008/0090942 A1* | 4/2008 | Hovorka | 523/200 |
| 2008/0196621 A1* | 8/2008 | Ikuno et al. | 106/31.13 |
| 2008/0291526 A1* | 11/2008 | Lin et al. | 359/296 |
| 2009/0035557 A1 | 2/2009 | Hartmann et al. | |
| 2011/0141522 A1 | 6/2011 | Vago | |
| 2013/0179996 A1* | 7/2013 | Boday et al. | 726/34 |
| 2014/0143881 A1* | 5/2014 | Boday et al. | 726/26 |

* cited by examiner

*Primary Examiner* — Vu Le
*Assistant Examiner* — Aklilu Woldemariam
(74) *Attorney, Agent, or Firm* — Isaac J. Gooshaw

(57) ABSTRACT

Exemplary embodiments of the present invention disclose a method for detecting a tampering event of a component. In a step, an exemplary embodiment encapsulates a fluorescent dye in one or more microcapsules. In another step, an exemplary embodiment embeds the one or more microcapsules in a translucent polymeric resin. In another step, an exemplary embodiment secures at least part of a component in the translucent polymeric resin. In another step, an exemplary embodiment detects a fluorescence of the fluorescent dye from a microcapsule in the translucent polymeric resin that is ruptured during a tampering with a light source that causes the fluorescent dye to fluoresce.

14 Claims, 6 Drawing Sheets

TAMPER DETECTION WITH MICROCAPSULE RUPTURE

FIELD OF THE INVENTION

The present invention relates generally to the detection of tampering with secure electronic components and more specifically to the use of microcapsules filled with a liquid that fluoresces under ultraviolet light when a capsule is ruptured during tampering.

BACKGROUND

Electronic devices whose physical security must be guaranteed, e.g., cryptographic and weapon-related devices, warrant special precautions against unauthorized physical access and undetected modification. Geographically dispersed manufacturing and assembly processes frequently result in many opportunities for unauthorized access, and after they are assembled and in operation, secure devices continue to require careful monitoring against unauthorized physical access. Physical access can result in circuit modification or an attachment of a monitoring device that can result in undetectable information leaks, a means to shut down a device's operation at will, and an opportunity to insert erroneous or misleading information into a secure information flow by an unauthorized entity.

Tamper evident techniques are less costly to implement than tamper prevention techniques, but both techniques are sometimes used concurrently. A tamper evident technique attempts to make a physical access to a device nearly impossible without leaving evidence of the access. Attractive tamper evident techniques provide an evidence of a tampering that is easily detectable without using expensive equipment or lengthy procedures while making the tampering impossible to accomplish without leaving such evidence. A tamper evident technique is even more attractive if a tampering entity remains oblivious to any evidence that his or her tampering creates, leaving several options open for security enforcement personnel to manage a tampering incident.

Some tamper evident techniques that are applied to electronic devices use mechanical enclosures and/or seals which are difficult to bypass without leaving evidence of a tampering event. However, these techniques increase weight which can be a factor in some implementations and they may require microscopic examination of an enclosure or a seal to detect a tampering. Also, they are less effective in an environment where sophisticated tools may be available to perform a tampering, subsequent to a physical interception of a device during manufacture, transportation, or storage, for example.

SUMMARY

Exemplary embodiments of the present invention disclose a method for detecting a tampering event of a component. In a step, an exemplary embodiment encapsulates a fluorescent dye in one or more microcapsules. In another step, an exemplary embodiment embeds the one or more microcapsules in a translucent polymeric resin. In another step, an exemplary embodiment secures at least part of a component in the translucent polymeric resin. In another step, an exemplary embodiment detects a fluorescence of the fluorescent dye from a microcapsule in the translucent polymeric resin that is ruptured during a tampering with a light source that causes the fluorescent dye to fluoresce.

DETAILED DESCRIPTION

In an exemplary embodiment, one or more microcapsules containing an ultraviolet dye (a UV dye) are formed using an oil-in-water emulsion technique to create a polymeric shell around a UV dye core. These microcapsules are then dispersed into a translucent polymeric resin which is then used to encapsulate a security component. A security component is an electronic component whose physical security must be guarded against a tampering and/or against an undetected tampering. When sufficiently compressed or punctured, cut, gouged, scratched, scraped, or otherwise penetrated, the one or more microcapsules rupture and release a UV dye material into the translucent polymeric resin. The UV dye from a ruptured microcapsule is irregular compared to a UV dye sphere within a non-ruptured microcapsule and can be visually identified under a UV lamp or by using a UV detecting instrument to determine that the one or more microcapsules have ruptured, thus indicating a tamper event.

Figure 1:
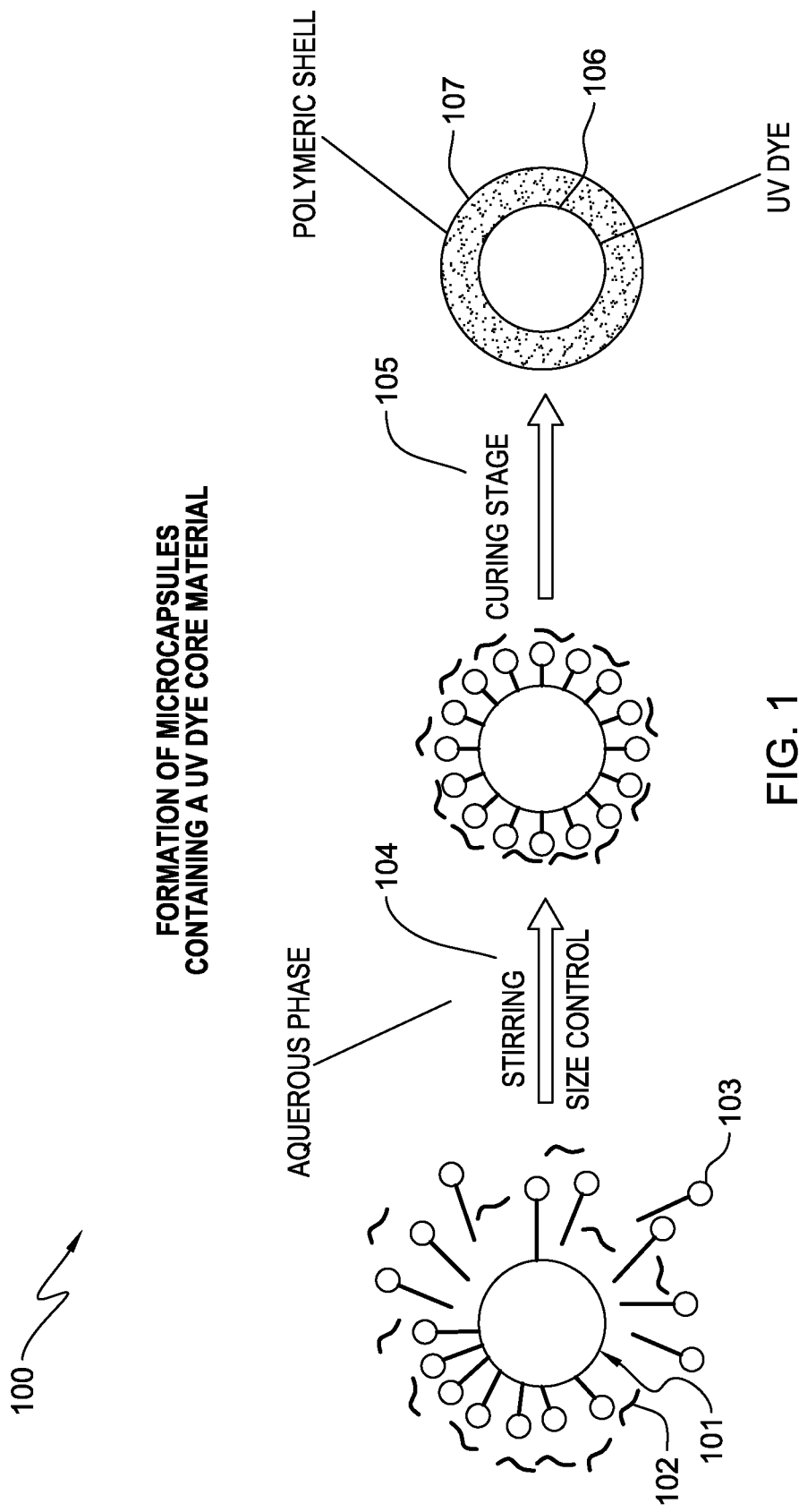
FIG. 1 depicts a formation of microcapsules containing a UV dye core material in accordance with one embodiment of the present invention.

In the exemplary embodiment one or more microcapsules are formed that contain a UV dye core material in a process 100 that is depicted in FIG. 1. A UV dye 101 (e.g., Anthracene, etc.) in an oil phase is dispersed in a solvent that is further dispersed into an aqueous continuous phase and stirred, which starts an emulsion process. A cross-linking agent 102 is introduced and reacts with a polymeric emulsifying agent 103 to generate a capsule wall around a UV dye particle. In one embodiment, UV dye particle size is controlled by adjusting a stir speed of the reaction in stirring and size control process 104 to produce a homogeneous UV dye particle size. In one embodiment, a higher stir speed results in smaller UV dye particles. Finally, a curing process 105 completes a reaction between cross-linking agent 102 and polymeric emulsifying agent 103 to form a spherical microcapsule with a UV dye core 106 surrounded by a polymeric shell 107.

Microcapsules are then embedded within a translucent polymeric resin (e.g., polyurethane, polypropylene, or polyethylene, etc.). A quantity of microcapsules made depends on a flow property of a polymeric resin used, a microcapsule size, and a desired density of microcapsules in the polymeric resin. A density of microcapsules desired is low enough to enable an irregular shape of a ruptured microcapsule or a regular shape of a non-ruptured microcapsule to be easily identified within a translucent polymeric resin, but high enough so a tampering event will rupture one or more microcapsules. Consequently a regular shape of a florescence from a non-ruptured microcapsule can be discriminated from an irregular shape of a florescence from microcapsule that is ruptured as a result of a tampering.

Several methods to detect a tampering can be performed, depending on whether or not an non-ruptured microcapsule is opaque, i.e., whether a florescence of a UV dye in a non-ruptured microcapsule is visible under UV light (as in a case of a non-opaque microcapsule) or not (as in a case of an opaque microcapsule). For example, in accordance with one embodiment, a camera can capture an image of a resin incorporating microcapsules and the image may be analyzed to detect a florescence from at least one ruptured microcapsule and signal a tampering. In such an embodiment, a microcapsule is opaque which requires a microcapsule to be ruptured before a florescence can manifest in a resin and therefore any detection of florescence by the camera indicates a tampering. A less expensive sensor may be used instead of a camera when a microcapsule is opaque since any florescence indicates a tampering. In another embodiment, a microcapsule is translucent, so a camera sees only non-ruptured microcapsules with sphere shaped florescence in an absence of a tampering, and in the presence of a tampering a camera sees sphere shaped florescence from non-ruptured microcapsules and irregular shaped florescence from ruptured microcapsules. An image processing technique is capable of classifying a shape of a viewed florescence as a smooth spherical shape or an irregular shape that indicates a tampering.

Figure 2:
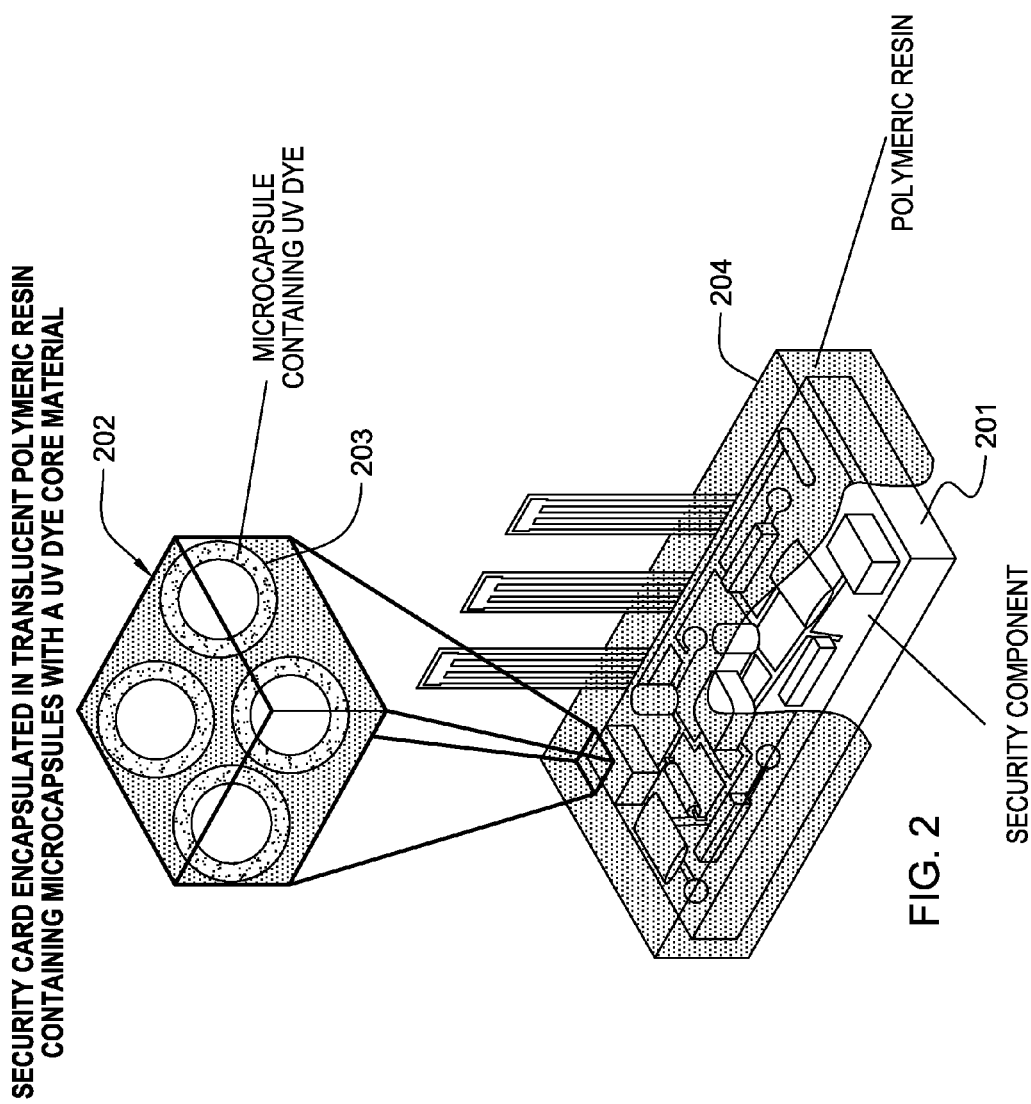
FIG. 2 depicts a security component that is encapsulated in a translucent polymeric resin containing microcapsules with a UV dye core material in accordance with one embodiment of the present invention.

FIG. 2 depicts a security component 201 that is given tamper evident protection. Security component 201 is encapsulated in a translucent polymeric resin 204. A sectional volume 202 of the polymeric resin 204 contains a microcapsule 203 that contains UV dye.

Figure 3:
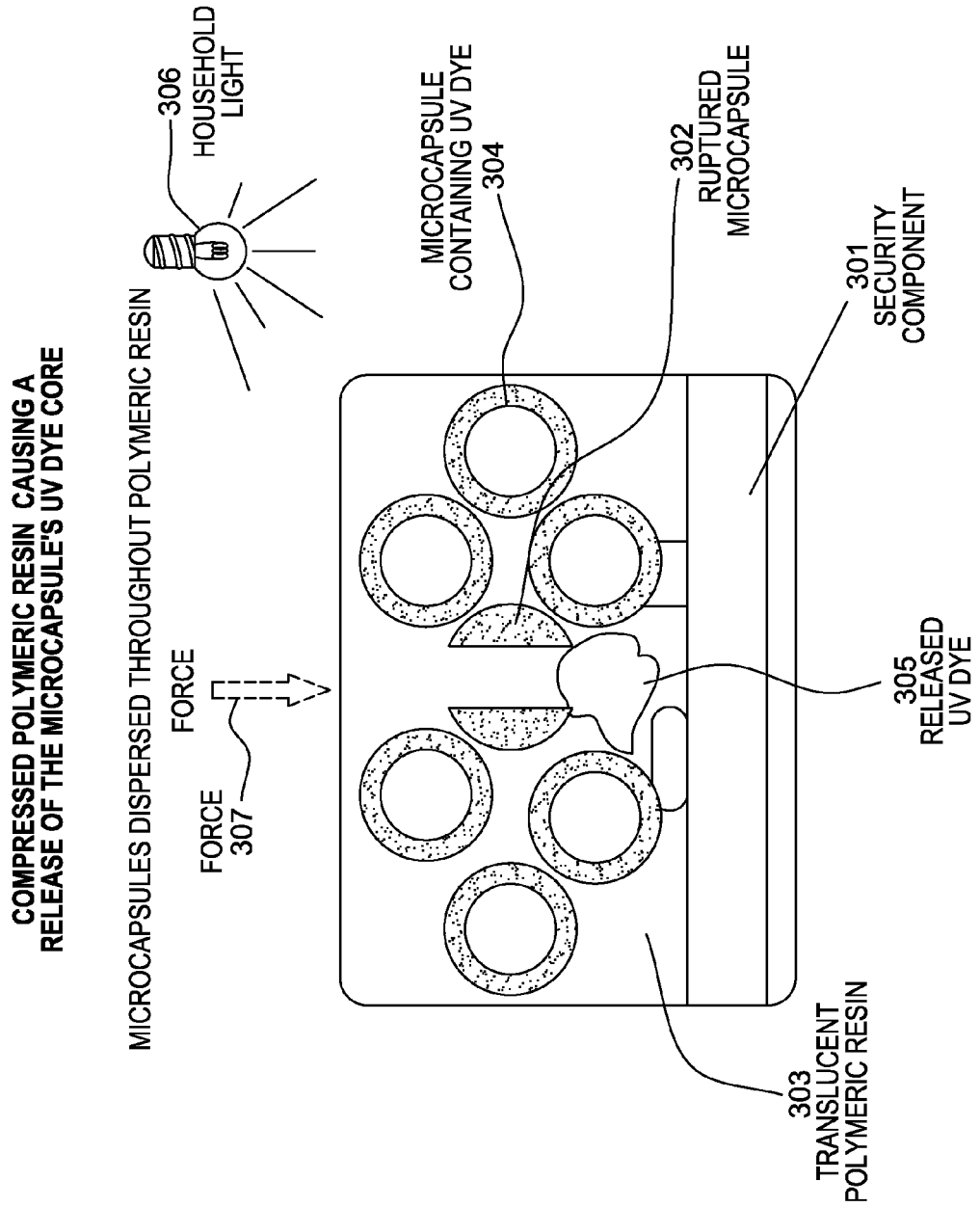
FIG. 3 depicts a compression of a translucent polymeric resin encapsulating a security component causing a release of the microcapsule's UV dye core under a household light in accordance with one embodiment of the present invention.

FIG. 3 depicts a ruptured microcapsule 302 in a translucent polymeric resin 303 that encapsulates a security component 301. A tampering force 307, (e.g., a force that results in a compression or a puncture, cut, gouge, scratch, or scrape of translucent resin 303), causes a microcapsule rupture and the ruptured microcapsule 302 releases a UV dye 305 into the translucent resin 303. Microcapsule 304 has not been ruptured by tampering force 307. Common indoor light, household light 306, does not fluoresce the released UV dye 305 and therefore an evidence of tampering is not apparent to a perpetrator of a tampering under common indoor lighting.

Figure 4:
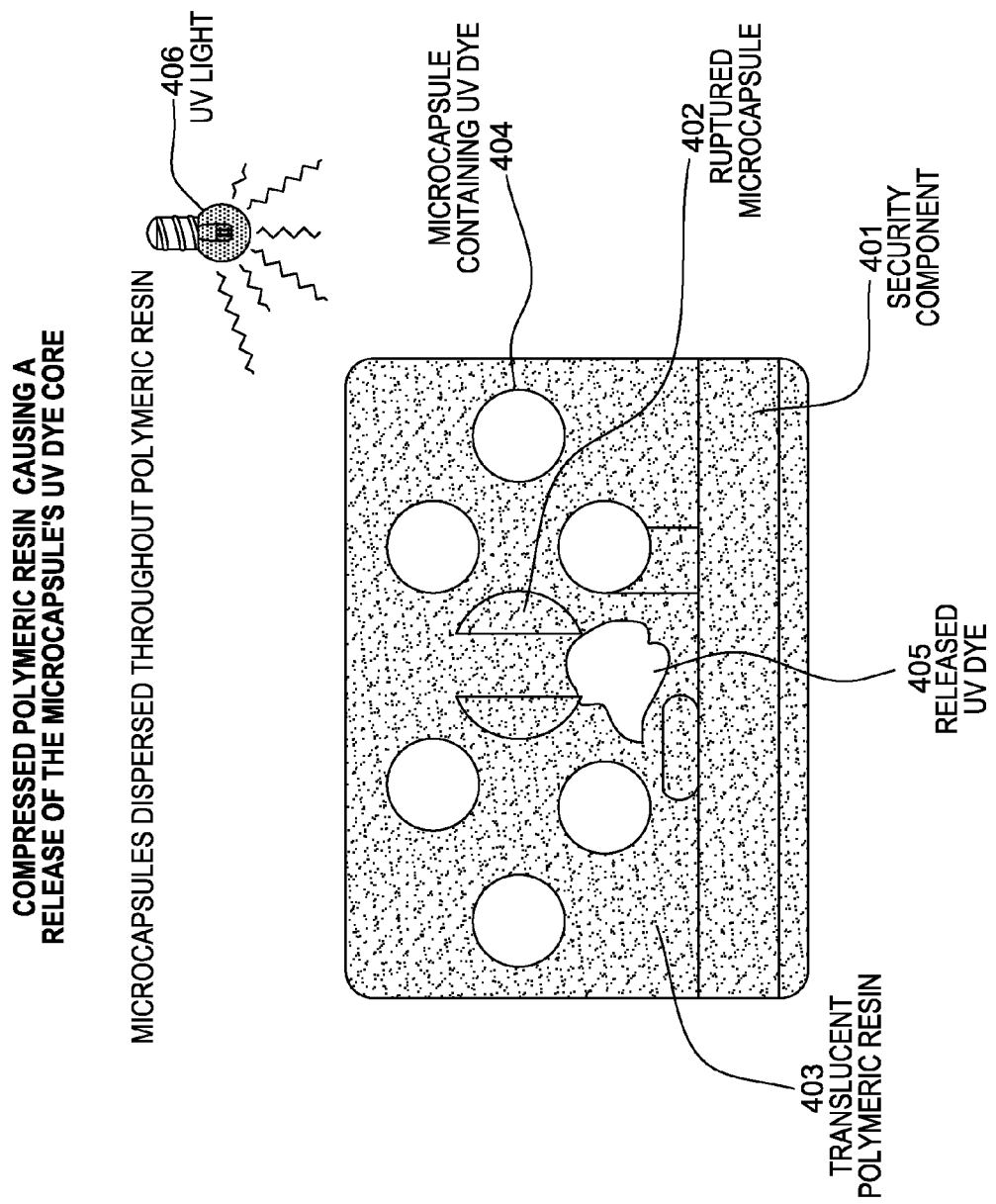
FIG. 4 depicts a compression of a translucent polymeric resin encapsulating a security component causing a release of the microcapsule's UV dye core under a UV light in accordance with one embodiment of the present invention.

FIG. 4 depicts a ruptured microcapsule 402 in a translucent polymeric resin 403 that encapsulates a security component 401 under UV light 406. A tampering force 307 has ruptured microcapsule 402 which releases a UV dye 405 into the translucent resin 403. Microcapsule 404 has not been ruptured by tampering force 307. A UV light 406 causes the released UV dye 405 to fluoresce in an irregular pattern which is an evidence of tampering that is readily detected.

Figure 5:
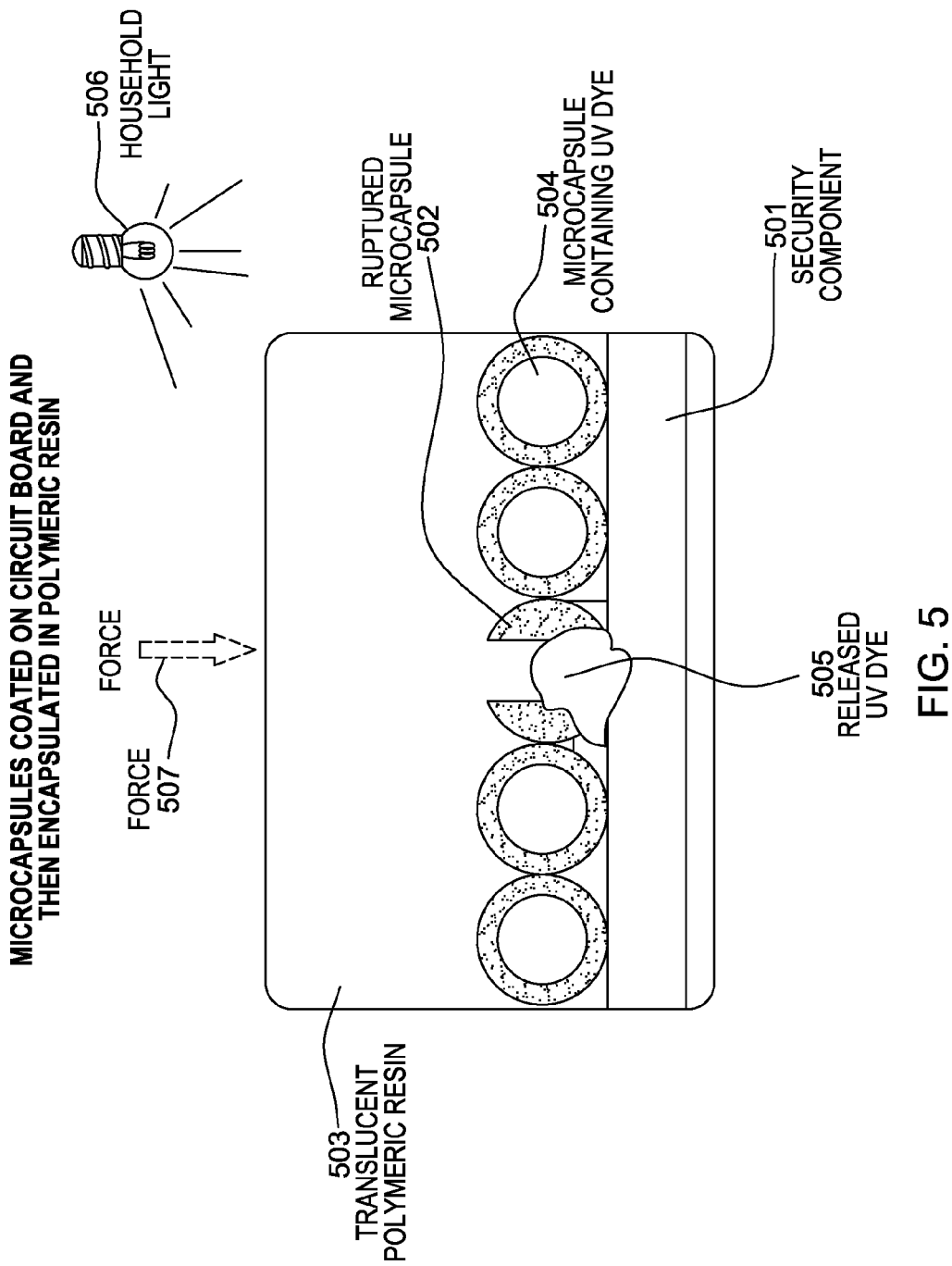
FIG. 5 depicts a compression of a translucent polymeric resin encapsulating a security component that is coated with one or more microcapsules causing a release of the microcapsule's UV dye core under a household light in accordance with one embodiment of the present invention.
Figure 6:
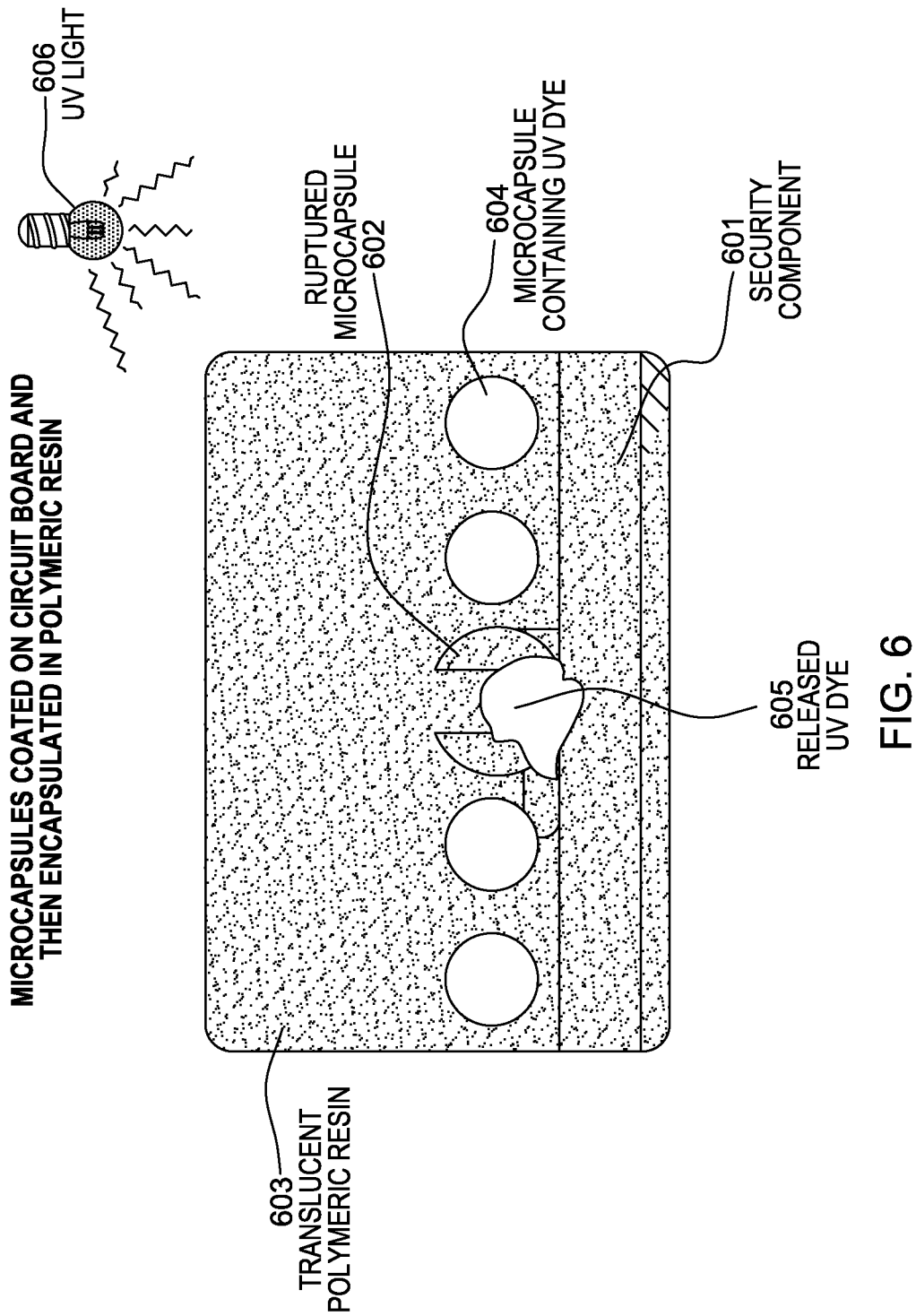
FIG. 6 depicts a compression of a translucent polymeric resin encapsulating a security component that is coated with one or more microcapsules causing a release of the microcapsule's UV dye core under a UV light in accordance with one embodiment of the present invention.

In another exemplary embodiment, depicted in FIG. 5 and FIG. 6, a security component is coated with one or more microcapsules and then the one or more microcapsules and the security component are encapsulated in a translucent polymeric resin (e.g., polyurethane, polypropylene, or polyethylene, etc.).

In the other exemplary embodiment, FIG. 5 depicts a ruptured microcapsule 502 in a translucent polymeric resin 503 that encapsulates a security component 501. A tampering force 507 causes a microcapsule rupture and the ruptured microcapsule 502 releases a UV dye 505 into the translucent resin 503. Microcapsule 504 has not been ruptured by tampering force 507. A household light 506 does not fluoresce the released UV dye 505 and therefore an evidence of tampering is not apparent to a perpetrator of a tampering.

In the other exemplary embodiment, FIG. 6 depicts a ruptured microcapsule 602 in a translucent polymeric resin 603 that encapsulates a security component 601 under UV light 606. A tampering force 507 has ruptured microcapsule 602 which releases a UV dye 605 into the translucent resin 603. Microcapsule 604 has not been ruptured by tampering force 507. A UV light 606 causes the released UV dye 605 to fluoresce and cause an evidence of tampering to be readily apparent.

The forgoing description are example embodiments only, and those skilled in the art understand that an infrared dye (e.g., Nickel(II) phthalocyanine) or other dye may be used, that a microcapsule that contains a dye may be made in many ways, and that entirely encapsulating a security component with a translucent polymeric resin is not always desired, and that a partial encapsulation or a coating of a portion of a security component may be desired. Those skilled in the art understand that microcapsules may be uniformly dispersed in a resin or concentrated in particular volumes in a resin or concentrated in particular volumes that constitute a pattern in a resin. In the forgoing descriptions, a word translucent denotes a range of transparencies that enable a microcapsule to be detected and that enable a dye from a microcapsule to be detected.

What is claimed is:

1. A method for detecting a tampering event of a component, the method comprising the steps of:
    encapsulating a fluorescent dye in one or more microcapsules, wherein the one or more microcapsules control detection of fluorescence of the fluorescent dye of the one or more microcapsules;
    embedding the one or more microcapsules in a translucent polymeric resin, wherein a number of the one or more microcapsules within a volume of translucent polymeric resin is configured to allow differentiation between one or more ruptured microcapsules and one or more non-ruptured microcapsules within the volume of translucent polymeric resin based, at least in part, on a detection of fluorescence of the fluorescent dye;
    securing at least part of a component in the translucent polymeric resin; and
    detecting a fluorescence of the fluorescent dye from a microcapsule in the translucent polymeric resin that is ruptured during a tampering with a light source that causes the fluorescent dye to fluoresce.

2. The method of claim 1, wherein the fluorescent dye includes one or more of an ultraviolet dye or an infrared dye.

3. The method of claim 1, wherein the one or more microcapsules form a pattern in the translucent polymeric resin.

4. The method of claim 1, wherein the securing the at least part of the component includes encapsulating the at least part of the component in the translucent polymeric resin.

5. The method of claim 1, wherein the securing the at least part of the component includes coating the at least part of the component in the translucent polymeric resin.

6. The method of claim 1, further comprising detecting a fluorescence of the fluorescent dye from a microcapsule in the translucent polymeric resin that is not ruptured with a light source that causes the fluorescent dye to fluoresce.

7. The method of claim 1, wherein the one or more microcapsules are opaque.

8. An apparatus for detecting a tampering event of a component, the apparatus comprising:
- a fluorescent dye encapsulated in one or more microcapsules, wherein the one or more microcapsules control detection of fluorescence of the fluorescent dye of the one or more microcapsules;
- a translucent polymeric resin containing the one or more microcapsules, wherein a number of the one or more microcapsules within a volume of translucent polymeric resin is configured to allow differentiation between one or more ruptured microcapsules and one or more non-ruptured microcapsules within the volume of translucent polymeric resin based, at least in part, on a detection of fluorescence of the fluorescent dye; and
- a layer of the translucent polymeric resin securing the component.

9. The apparatus of claim 8, wherein the fluorescent dye includes one or more of an ultraviolet dye or an infrared dye.

10. The apparatus of claim 8, wherein the one or more microcapsules form a pattern in the translucent polymeric resin.

11. The apparatus of claim 8, wherein the securing the at least part of the component includes encapsulating the at least part of the component in the translucent polymeric resin.

12. The apparatus of claim 8, wherein the securing the component includes coating the component in the translucent polymeric resin.

13. The apparatus of claim 8, wherein the fluorescent dye from a microcapsule in the translucent polymeric resin that is not ruptured will fluoresce with a light source.

14. The apparatus of claim 8, wherein the one or more microcapsules are opaque.

\* \* \* \* \*